United States Patent
Manera (10) Patent No.: US 10,993,633 B2
(45) Date of Patent: *May 4, 2021

(54) REMOTE AMBULATORY CARDIAC MONITORING SYSTEM FOR ACQUIRING ECG SIGNALS

(71) Applicant: Applied Cardiac Systems, Inc., Irvine, CA (US)

(72) Inventor: Loren A. Manera, Laguna Hills, CA (US)

(73) Assignee: ACS DIAGNOSTICS, INC., Irvine, CA (US)

(*) Notice: Subject to any disclaimer, the term of this patent is extended or adjusted under 35 U.S.C. 154(b) by 68 days.

This patent is subject to a terminal disclaimer.

(21) Appl. No.: 15/804,888

(22) Filed: Nov. 6, 2017

(65) Prior Publication Data

US 2018/0055383 A1 Mar. 1, 2018

Related U.S. Application Data

(63) Continuation of application No. 14/990,707, filed on Jan. 7, 2016, now Pat. No. 9,808,165, which is a
(Continued)

(51) Int. Cl.
| | | |
|---|---|---|
| *A61B 5/0245* | (2006.01) | |
| *A61B 5/0452* | (2006.01) | |
| *A61B 5/046* | (2006.01) | |
| *A61B 5/0464* | (2006.01) | |
| *A61B 5/00* | (2006.01) | |

(Continued)

(52) U.S. Cl.
CPC .......... *A61B 5/0245* (2013.01); *A61B 5/0006* (2013.01); *A61B 5/276* (2021.01); *A61B 5/304* (2021.01); *A61B 5/316* (2021.01); *A61B 5/332* (2021.01); *A61B 5/333* (2021.01); *A61B 5/349* (2021.01); *A61B 5/361* (2021.01); *A61B 5/363* (2021.01); *A61B 5/6823* (2013.01); *A61B 2505/07* (2013.01); *A61B 2560/0431* (2013.01)

(58) Field of Classification Search
CPC . A61B 5/0006; A61B 5/0245; A61B 5/04012; A61B 5/0404; A61B 5/0424; A61B 5/04288; A61B 5/0432; A61B 5/0452; A61B 5/046; A61B 5/0464; A61B 5/6823; A61B 2505/07; A61B 2560/0431
USPC ......................................................... 600/509
See application file for complete search history.

(56) References Cited

U.S. PATENT DOCUMENTS 4,230,127 A * 10/1980 Larson ................ A61B 5/0404
600/382
5,544,661 A * 8/1996 Davis ................... A61B 5/0002
600/513

(Continued)

*Primary Examiner* — Mark Bockelman
(74) *Attorney, Agent, or Firm* — Steptoe & Johnson LLP (57) ABSTRACT

A system and method for a multi-function remote ambulatory cardiac monitoring system. The system includes a housing and a microprocessor disposed within the housing. The microprocessor controls the remote ambulatory cardiac monitoring system. The system also includes an electrode for sensing ECG signals and the electrode being in communication with the microprocessor. An integrated cellular module also is included in the system, and the cellular module is connected to the microprocessor and disposed within the housing. The integrated cellular module transmits ECG signals to a remote center.

4 Claims, 4 Drawing Sheets

Related U.S. Application Data continuation of application No. 14/617,688, filed on Feb. 9, 2015, now Pat. No. 9,237,859, which is a continuation of application No. 13/861,322, filed on Apr. 11, 2013, now Pat. No. 8,972,000, which is a continuation of application No. 12/938,268, filed on Nov. 2, 2010, now abandoned.

(60) Provisional application No. 61/257,388, filed on Nov. 2, 2009.

(51) Int. Cl.

| | | |
|---|---|---|
| *A61B 5/04* | (2006.01) | |
| *A61B 5/0404* | (2006.01) | |
| *A61B 5/0428* | (2006.01) | |
| *A61B 5/0432* | (2006.01) | |
| *A61B 5/0424* | (2006.01) | |
| *A61B 5/276* | (2021.01) | |
| *A61B 5/304* | (2021.01) | |
| *A61B 5/316* | (2021.01) | |
| *A61B 5/332* | (2021.01) | |
| *A61B 5/333* | (2021.01) | |
| *A61B 5/349* | (2021.01) | |
| *A61B 5/361* | (2021.01) | |
| *A61B 5/363* | (2021.01) | |

(56) References Cited

U.S. PATENT DOCUMENTS

| | | | |
|---|---|---|---|
| 5,640,966 A | 6/1997 | Heden et al. | |
| 6,546,232 B1* | 4/2003 | Sack | A61B 5/0006 342/57 |
| 6,551,252 B2* | 4/2003 | Sackner | A61B 5/0205 600/536 |
| 6,647,286 B1 | 11/2003 | Kato | |
| 7,433,731 B2 | 10/2008 | Matsumura et al. | |
| 7,940,168 B2* | 5/2011 | Needham | G08B 25/014 340/539.12 |
| 8,116,841 B2* | 2/2012 | Bly | A61B 5/0205 600/391 |
| 8,972,000 B2* | 3/2015 | Manera | A61B 5/0404 600/509 |
| 9,237,859 B2* | 1/2016 | Manera | A61B 5/0404 |
| 9,662,030 B2* | 5/2017 | Thng | A61B 5/04085 |
| 9,808,165 B2* | 11/2017 | Manera | A61B 5/0404 |
| 2002/0045837 A1 | 4/2002 | Wei et al. | |
| 2002/0143576 A1 | 10/2002 | Nolvak et al. | |
| 2005/0250440 A1* | 11/2005 | Zhou | G01S 5/0027 455/12.1 |
| 2006/0004295 A1 | 1/2006 | Prydekker | |
| 2008/0027338 A1* | 1/2008 | Lu | A61B 5/0424 600/509 |
| 2008/0177341 A1 | 7/2008 | Bowers | |
| 2009/0240297 A1* | 9/2009 | Shavit | A61N 1/39 607/5 |
| 2011/0060378 A1 | 3/2011 | Tuysserkani | |
| 2011/0112418 A1* | 5/2011 | Feild | A61B 5/0006 600/509 |

\* cited by examiner

REMOTE AMBULATORY CARDIAC MONITORING SYSTEM FOR ACQUIRING ECG SIGNALS

CROSS-REFERENCE TO RELATED CASES

This application is a continuation of U.S. application Ser. No. 14/990,707, filed Jan. 7, 2016, now U.S. Pat. No. 9,808,165, which is a continuation of U.S. application Ser. No. 14/617,688, filed Feb. 9, 2015, now U.S. Pat. No. 9,237,859, which is a continuation of U.S. application Ser. No. 13/861,322, filed Apr. 11, 2013, now U.S. Pat. No. 8,972,000, which claims priority to U.S. application Ser. No, 12/938,268, filed Nov. 2, 2010, now abandoned, which claims priority to U.S. Provisional patent application 61/257,388, filed Nov. 2, 2009, the entire disclosures of which are hereby incorporated by reference.

FIELD OF THE DISCLOSURE

The present disclosure relates generally to the field of portable health monitors and more specifically to battery operated multi-function EKG recorder/transmitters.

BACKGROUND

If you or your doctor have concerns about the function of your heart or other similar organ you may embark on a multi-step evaluation that may include many different tests for example a resting 12-lead EKG test, an EKG stress test, a 24-hour Holter monitor evaluation and or a 30-day MCT/Event monitoring. These tests and others utilize many different and specialized tools due to some of the conflicting requirements of the tests or the equipment. For example, some of the tests must be done in a doctor's office or a hospital or lab because of the cost and power consumption of the test tools and it would be unrealistic to conduct a 30-day MCT analysis with the patient confined to the hospital, or worse, the doctor's office.

Some of the evaluation tests are also challenging because of the limitations enforced by the ability of the medical system to derive adequate compensation for the work necessary. For example, an MCT monitor analysis of a patient may be conducted for up to 30 days. The equipment to perform this monitoring and analysis must be portable, low-power, durable and accurate. The necessity of low-power and durable equipment forces the equipment designers to cut corners on real-time data analysis. As a result, many false positive events generate excessive data that requires expensive medical professional time to review. Thus, the doctor ordering the test (and the insurance company looking over his shoulder) must be cognizant that the test, and the analysis of the resulting data could cost more than anyone will be paid to perform the test.

SUMMARY

Briefly, and in general terms, disclosed herein is a multi-function health monitor. By way of example only, the multi-function health monitor is capable of calculating 1 to 12 channels or leads of ECG data using only three (to twelve) electrodes connected to the patient. It has been contemplated that the lead switching technique allows a capture of ECG data with the noise cancellation benefits of a right leg feed system. In one embodiment, use of only three electrodes makes the multi-function health monitor ideal for ambulatory data gathering and to enable better long-term compliance by patients. In one embodiment, the multi-function health (MFH) monitor may be capable of performing a resting 12-lead EKG test, an EKG stress test, a 24-hour Holter monitor evaluation, and a 30-day MCT/Event study, as well as providing both resting and ambulatory blood pressure monitoring through the use of an auxiliary sensor.

The MFH monitor can acquire and provide data analysis through control electronics or a gate array in one embodiment. Data may also be stored for remote analysis as well as for transmission to remote stations upon occurrence of one or more threshold events. Parameters for threshold events may be adjusted remotely to obviate the need for a patient to travel for system adjustment.

The design of the control electronics or gate array and the data algorithms permits one or more sections of the control electronics or gate array to be powered off when unused to prevent unnecessary power drain. The data algorithms implemented in the hardware of the control electronics or gate array permits a high level of sophisticated data processing by the remote ambulatory cardiac monitoring system as data is acquired to minimize false events and minimize the requirement for remote data analysis.

A lead resistivity measurement system quantifies and may compensate for increasing resistance between an electrode and the patient that results from the length of time the electrodes are installed on a patient. This system may also detect and alert to an electrode disconnected.

In yet another embodiment, a remote ambulatory cardiac monitoring system includes a microprocessor for controlling the remote ambulatory cardiac monitoring system. The system also includes a non-transitory computer readable medium associated with the microprocessor. The non-transitory computer readable medium includes instructions to perform an EKG mode, ECG Holter mode, and MCT mode. The EKG mode may be a resting EKG mode or an EKG stress test. Further, the system includes a controller connected to the microprocessor. The controller switches the functionality of the remote ambulatory cardiac monitoring system by causing the microprocessor to initiate one of the EKG mode, ECG Holter mode, or MCT/Event mode.

In another embodiment, the non-transitory computer readable medium associated with the microprocessor includes instructions for a USB data transfer mode. The system also includes a plurality of electrodes secured to a patient, each electrode operably connected to an input/output cable for sensing ECG signals from the patient. In one embodiment, the controller includes a hardware gate array for controlling acquisition of ECG signals through the input/output cable. The system may include a cable socket connected to the controller. The cable socket receives the input/output cable.

By way of example only, the controller may switch the functionality of the remote ambulatory cardiac monitoring system to the MCT/Event mode when a three-electrode cable is connected to the cable socket. Also by way of example only, the controller switches the functionality of the remote ambulatory cardiac monitoring system to the EKG mode when a multi-wire electrode cable is connected to the cable socket. Specifically, the controller may switch the functionality to the EKG mode when an eight, ten, or twelve electrode cable is connected to able socket of the system. Also, the controller may switch the functionality of the remote ambulatory cardiac monitoring system to the ECG Holter mode when a five electrode cable is connected to the cable socket. In one embodiment, the controller automatically switches the functionality of the remote ambulatory cardiac monitoring system from the ECG Holter mode to the MCT/Event mode if the ECG Holter mode is negative after a period. For example, the controller automatically switches the functionality of the remote ambulatory cardiac monitoring system from the ECG Holter mode to the MCT/Event mode if the ECG Holter mode is negative after at least a 24 hour period.

In yet another embodiment, a method for controlling the functionality of a monitoring device includes detecting the selection of one of a plurality of modes on the monitoring device. The plurality of modes on the monitoring device including EKG mode, ECG Holter mode, and MCT/Event mode. The EKG mode may be a resting EKG mode or an EKG stress test. Further, the method includes initiating one of the EKG mode, ECG Holter mode, and MCT/Event mode. The plurality of modes on the monitoring device may include a USB data transfer mode.

In one embodiment, detecting the selection of one of a plurality of modes on the monitoring device includes detecting a type of electrode cable inserted into the monitoring device. By way of example only, the method may switch the functionality of the monitoring device to the MCT/Event mode when a three-electrode cable is detected by the monitoring device. Also, the method may switch the functionality of the monitoring device to the EKG mode when a multi-electrode cable is detected by the monitoring device. The method may switch the monitoring device to the EKG mode when an eight, ten, or twelve electrode cable is detected. Further, in one embodiment, the method switches the functionality of the monitoring device to the ECG Holter mode when a five-electrode cable is detected by the monitoring device. Also, the method may include determining that the ECG Holter mode is negative for a set period of time and automatically switching the functionality of the monitor device from the ECG Holter mode to the MCT/Event mode. As an example, if the ECG Holter mode is negative for at least a 24 hour period, then the method automatically switches the functionality of the monitor device from the ECG Holter mode to the MCT/Event mode. In one embodiment, the method switches the functionality of the monitoring device by causing a microprocessor in the monitoring device to initiate one of the EKG mode, ECG Holter mode, and MCT/Event mode.

In yet another embodiment, a remote ambulatory cardiac monitoring system includes a monitoring device having a housing. A microprocessor is stored within the housing of the monitoring device and the system includes a non-transitory computer readable medium associated with the microprocessor. The non-transitory computer readable medium includes instructions to perform EKG mode, ECG Holter mode, and MCT/Event mode. Further, the system includes a controller stored within the housing of the monitoring device and connected to the microprocessor. The controller may switch the functionality of the remote ambulatory cardiac monitoring system by causing the microprocessor to initiate one of the EKG mode, ECG Holter mode, and MCT/Event mode.

These and other features and advantages will become further apparent from the detailed description and accompanying figures that follow. In the figures and description, numerals indicate the various features of the disclosure, like numerals referring to like features throughout both the drawings and the description.

DETAILED DESCRIPTION OF THE PREFERRED EMBODIMENTS

In electrocardiography, the word "lead" may refer to either the electrodes attached to the patient, or, properly, to the voltage or signal measured between two electrodes. To avoid confusion, "channel" is used to describe the voltage, signal or view from a positive electrode to a negative electrode across the heart.

Figure 1:
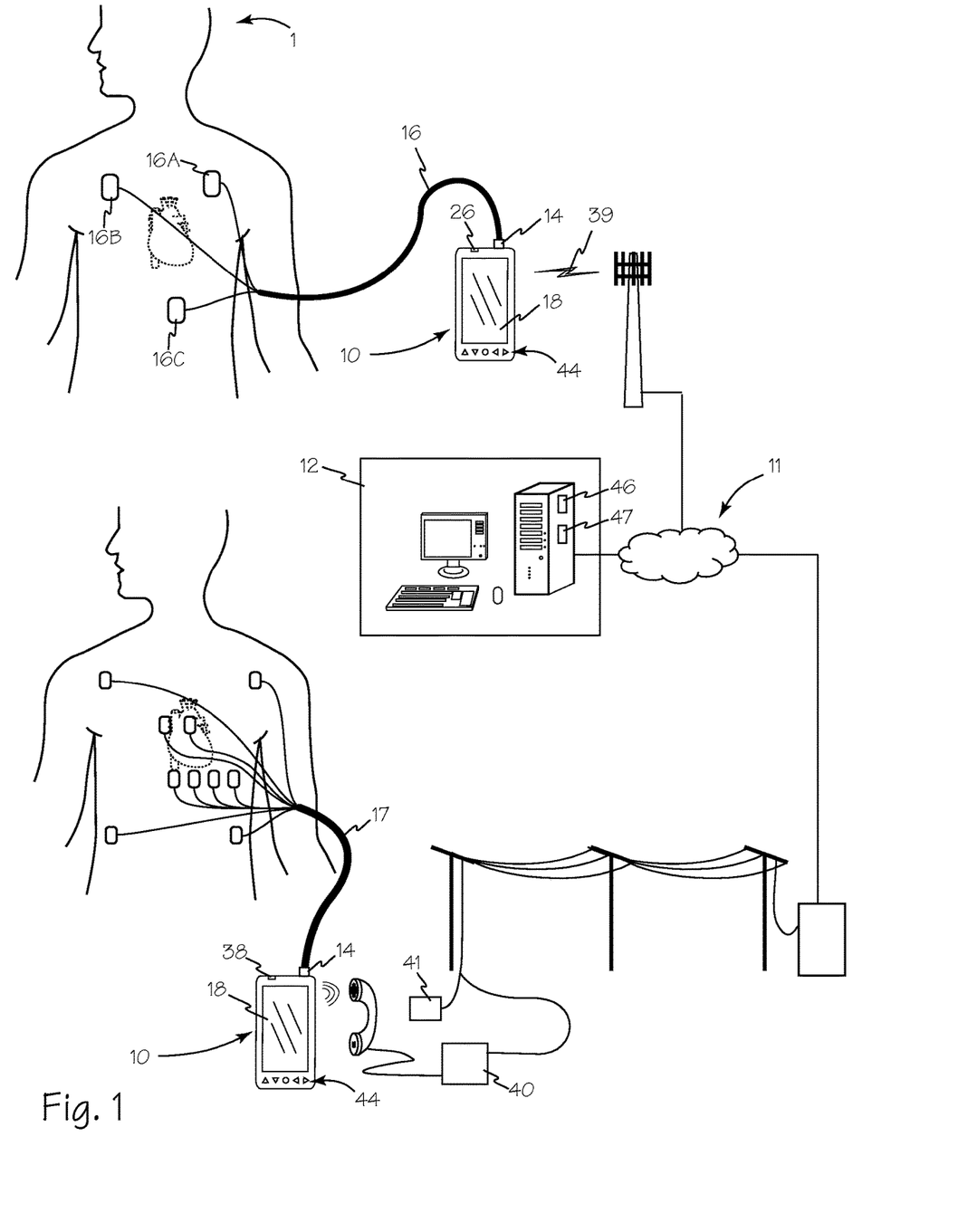
FIG. 1 is a block diagram of multifunction health monitor systems with alternate electrode sets and the system network.

Referring now to FIG. 1, a remote ambulatory cardiac monitoring system 10 is a multi-purpose ECG recorder, arrhythmia detector and alarm, capable of changing its functionality to meet the normal workflow of a Cardiologist office. For a patient of concern such as patient 1, a cardiologist might first order a resting 12-channel EKG study. If the study is negative, then a 24-hour Holter would be prescribed next. If the Holter study is still negative then a mobile cardiac telemetry (MCT) study might be performed for up to 30 days.

Remote ambulatory cardiac monitoring system 10 can perform all of these functions as individual instruments have done in the past and can change the way these tests are usually performed. A single instrument can save money and improve patient compliance particularly when going from a Holter to a MCT recorder because a new apparatus is not necessary. Because of the built-in cellular modem technology, patient demographic and scheduling information can be "pushed" from an EMR or HIS system to system 10 over a network such as network 11.

Conversely, test results can automatically be sent back the electronic management system of a 24-hour monitoring service such as remote monitoring service 12. Monitoring system 10 is "smart" in that it automatically adapts to its intended purpose by detecting the EKG electrode set or other cable inserted into cable socket 14. For example, insertion of a three-electrode cable 16 may cause monitoring system 10 to initiate MCT/Event mode. Insertion of ten-electrode cable 17 may cause monitoring system 10 to initiate EKG mode, such as 12-lead EKG mode. Remote ambulatory cardiac monitoring system 10 may also provide video tutorials and other information on display screen 18 related to electrode connection, specific to the modality and can also provide real-time ECG arrhythmia detection using its built-in hardware DSP engine in any mode: resting 12-lead EKG mode, Holter mode, or MCT/Event mode.

Monitoring system 10 also integrates various ECG-specific functions that are well suited for scalable electrocardiogram (ECG) applications. The device may also be used in high-performance, multichannel data acquisition system by powering down the ECG-specific circuitry in the controller.

Figure 3:
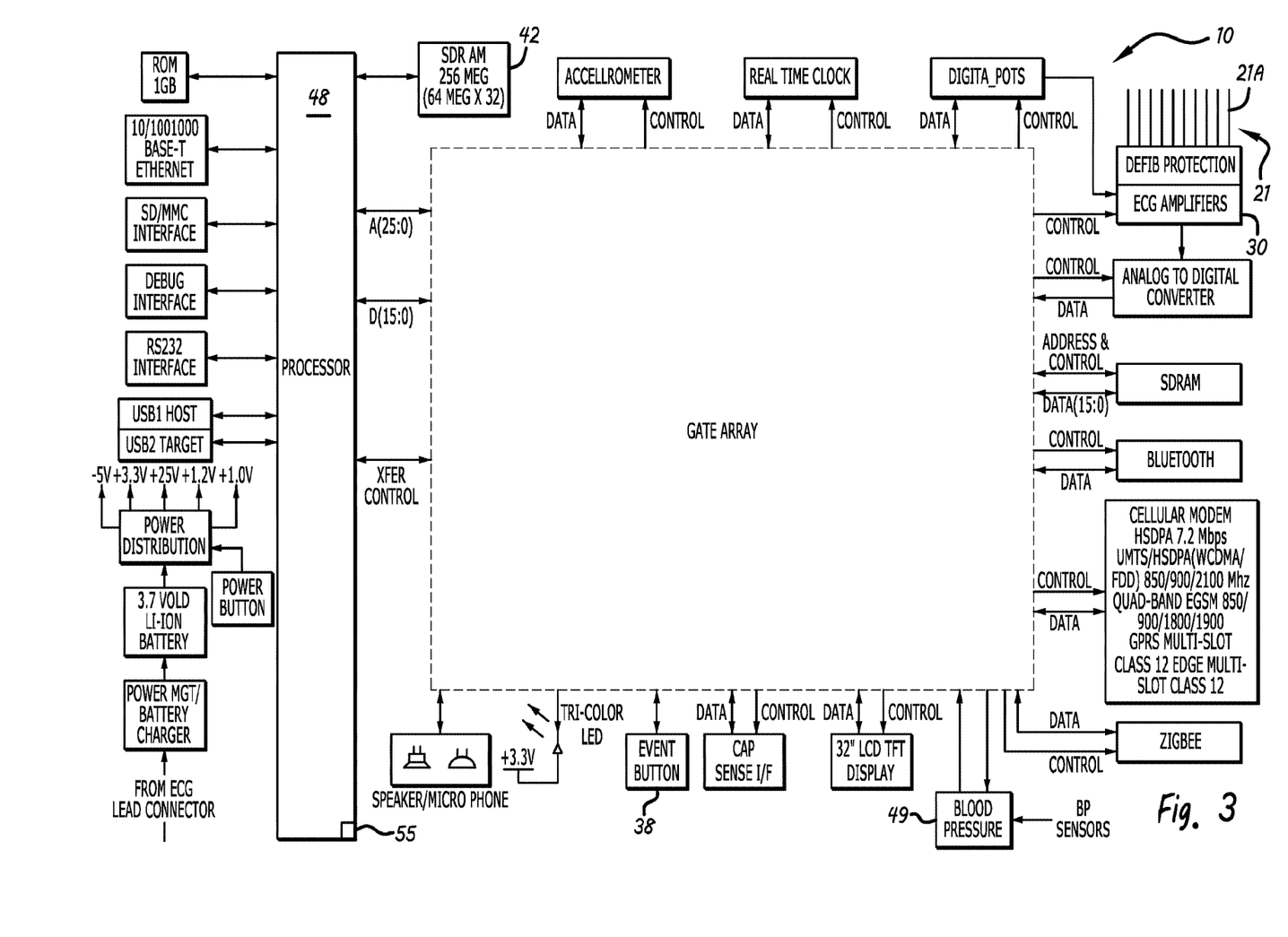
FIG. 3 is a block diagram of the gate array controller and connected components of the remote ambulatory cardiac monitoring system of FIG. 1.

Referring now to FIG. 3, in one embodiment, a controller 20 has a highly programmable multiplexer that allows for temperature, supply, input short, and RLD measurements. Additionally, a multiplexer allows any of input electrode lines 21 such as electrode line 21A to be programmed as the patient reference drive. The PGA gain may be chosen from one of seven settings (1, 2, 3, 4, 6, 8, and 12). The ADCs in the device offer data rates from 250 SPS to 32 kSPS.

Communication to the device is accomplished using an SPI-compatible interface. The device provides four GPIO pins for general use. Multiple devices may be synchronized using the START pin.

The internal reference can be programmed to either 2.4V or 4V. The internal oscillator generates a 2.048 MHz clock. The versatile right leg drive (RLD) block allows the user to choose the average of any combination of electrode lines 21 to generate the patient drive signal for signal noise reduction.

Figure 2:
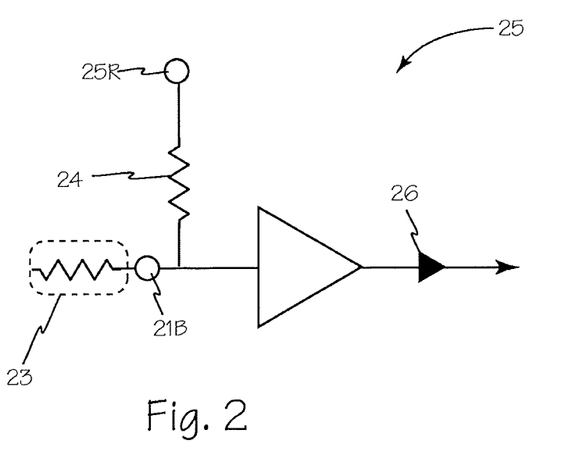
FIG. 2 is a schematic diagram of an electrode input.

Referring now to FIG. 2, leadoff detection and electrode analysis can be accomplished either by using a pull-up/pull-down resistor or a current source/sink such as the voltage divider formed by electrode 23 and reference resistor 24 of electrode input channel 25. A fixed voltage or current is applied at reference point 25R and electrode 23 is connected at input point 21B. As electrode 23 separates from the patient's skin and/or the electrode adhesive decays, the resistance between electrode 23 and the patient will grow relative to reference resistor 24. Controller 20 can quantify the change of electrode resistance and adjust signal gain to compensate until the electrode separates from the patient. Input signal 26 may be analyzed for the contribution of reference voltage or current at reference point 25R and if signal 26 is entirely the reference voltage or current, a leadoff alarm is initiated.

Monitoring system 10 supports both hardware pace detection and software pace detection. The Wilson center terminal (WCT) block can be used to generate the WCT point of the standard 12-lead EKG.

Remote ambulatory cardiac monitoring system 10 is a multipurpose device designed with the ability to perform: a 3-channel (3-electrode) Mobile Cardiac Telemetry complete with Arrhythmia Detection and Alarm for up to 30 days; a 24-hour or longer 12-channel or 3-channel (5-electrode) ECG Holter study; and a resting 12-channel EKG. The device may be used for patient in home use with remote clinician data analysis as well as use within the office or home setting by a medical professional.

Remote cardiac monitor 10 includes:

1) a single component EKG monitor with an integrated cellular modem and 2) an interface to five independent cable configurations through a single connector. Monitor 10 automatically changes functionality when a specific cable with the same form factor is inserted with the following configurations:

3-wire, ambulatory, snap electrode cable invokes a 1, 2, or 3-channel MCT/Event mode (Lead I, II, III—no anterior views)

10-wire, ambulatory, snap electrode cable invokes the Holter 12-channel mode 5-wire, ambulatory, snap electrode cable invokes the Holter 3-channel mode by default (up to 7-leads are available with anterior views); If programmed to do so, the system can automatically switch to the MCT/Event mode after 24-or more hours 10-wire, resting (lengthened for full body), clip electrode cable invokes the Resting 12-lead EKG mode (8-channels; Lead III, aVF, aVR, aVL derived)

4-wire, USB cable invokes the PC communication service mode. Cable is interchangeable with EKG lead sets requiring disconnection from the body before connection to an external device can be made.

The built-in cellular modem technology pushes and pulls information to and from the device in a HIPAA compliant fashion using the cryptographic protocol; Transport Layer Security (TLS). Additional data integrity is performed by Error Correction Coding (ECC) and MD5 hash sums.

Monitor 10 houses a microprocessor for running the algorithm and an application specific integrated circuit (ASIC) as controller 20, a rechargeable battery, real time ECG arrhythmia detection using built-in hardware DSP engine in any mode, ECG capture circuitry provided by the ASIC and the multiple components, GSM/GPRS/EGPRS/WCDMA/HSPA Upon detection of an arrhythmic or patient-activated event through activation of patient, the ECG signal is transmitted wirelessly via the cellular network to a remote monitoring center for additional analysis and intervention by a clinician. When cellular service is unavailable, the event will be stored until such time the cellular network becomes available or the patient transmits the data using a land telephone line.

If in the resting 12-lead mode, the device can capture, display, and analyze 12 channels of ECG for up to 1,024 patients in diagnostic quality. The ECG can be streamed in real-time to a computer wirelessly via the 802.15.4 network transceiver to be displayed, printed, and stored. An embedded SQL database is used in monitor 10 for ECG storage and reporting in all modes—MCT, Holter, and resting 12-lead as well as storage of other data such as blood pressure data.

Figure 4:
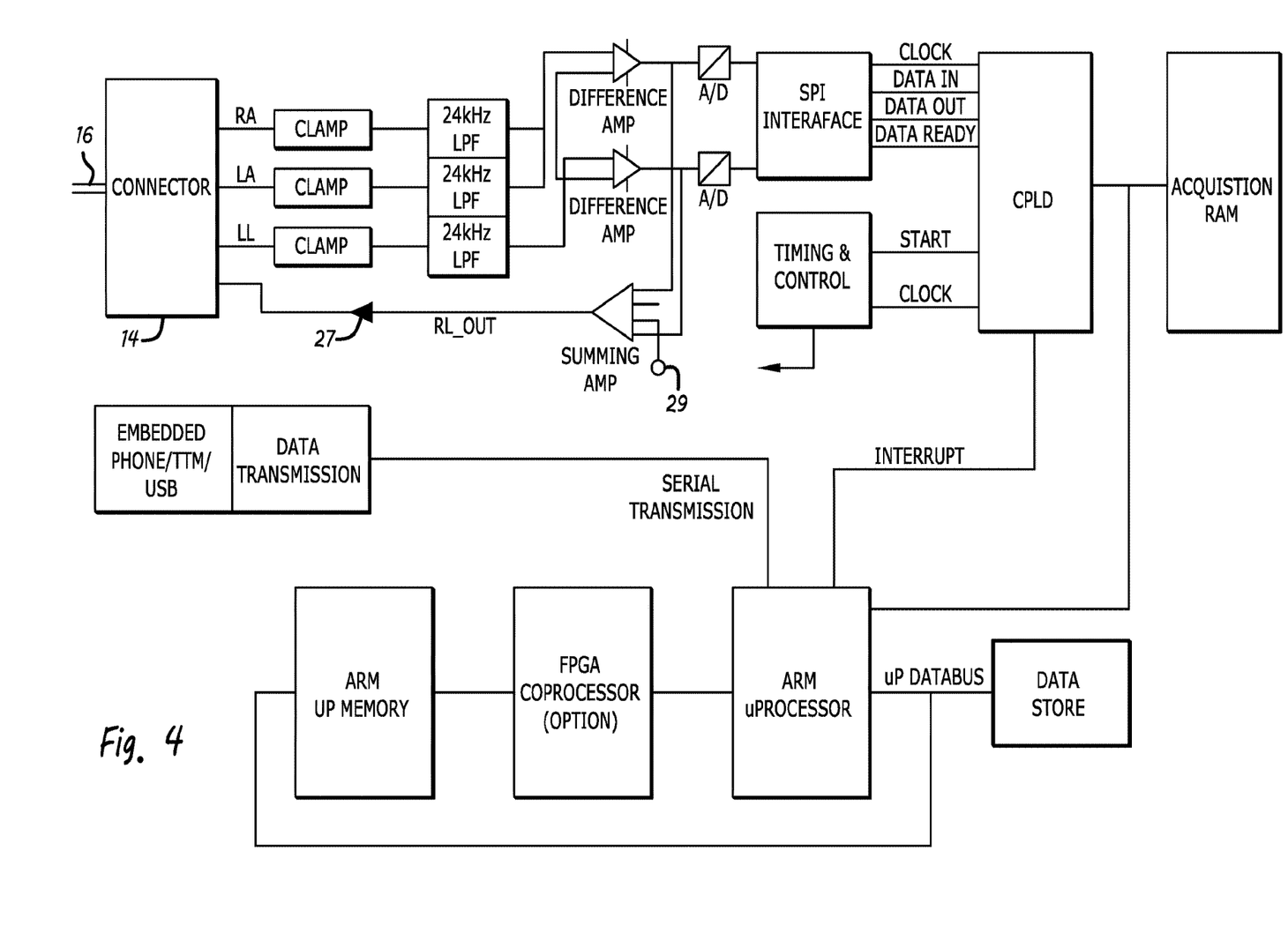
FIG. 4 is a block diagram of the timing and data paths of a remote ambulatory cardiac monitoring system.

Conventional 3-lead electrode systems provide a single channel measurement with no redundancy. Referring now to FIGS. 1 and 4, the MCT/Event mode of remote ambulatory cardiac monitoring system 10 is initiated by connection of cable 16 which uses three electrodes, electrodes 16A, 16B and 16C, configured as RA (Right Arm), LA (Left Arm) and LL (Left Leg) to calculate Lead I (channel I), Lead II (channel II), or Lead III(channel III). Controller 20 dynamically substitutes RL (Right Leg) drive 27 for each electrode as it makes a measurement across the other two electrodes. This allows the system to function as if it were a four electrode system making use of the noise cancellation of the RL output. The RL drive also has an integrated constant current source 29 which can be momentarily switched on to make an impedance measurement of each connected electrode. This allows system to make an immediate leadoff or high impedance (HiZ) determination and use the remaining two electrodes to make a single lead measurement. Controller 20 can measure and calculate six separate data channels (Lead I, Lead II, Lead III, aVL, aVR, and aVF) with the effect of full AC noise cancellation via the RL drive provided to each of the three electrodes are connected. In the case of any electrode becoming disconnected, the system will still function as a single channel system.

Figure 5:
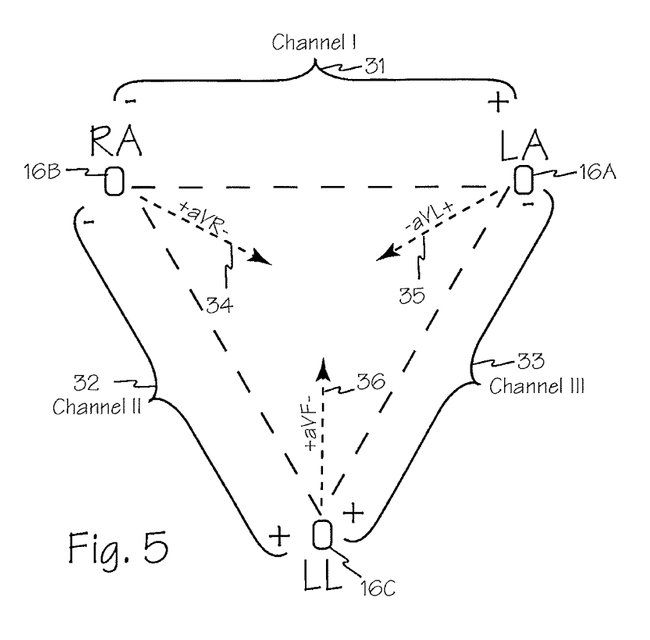
FIG. 5 is a block diagram for channel derivation from three electrodes.

RL drive 27 sums the ECG signals from two of the three electrodes, the LA, RA, and LL electrodes, and applies the combined signal 180 degrees out of phase and drives the resulting inverted signal, signal 27, back into the patient for noise cancellation. In MCT/Event mode, remote ambulatory cardiac monitoring system 10 only uses three electrodes such as electrodes 16A, 16B and 16C, as shown in FIG. 5, so the fourth electrode (RL) has to replace one of the limb lead electrodes dynamically. This done by electronically switching the LL input circuitry in ECG instrumentation amplifier 30, shown in FIG. 3, with the RL output drive circuitry. The LA-RA (channel I) measurement orientation is show in FIG. 5 as channel 31. LL Electrode circuitry is replaced by the RL circuitry.

Controller 20 electronically switches the LA input circuitry in ECG instrumentation amplifier 30 with the RL output drive circuitry. The RA-LL (channel II) measurement orientation is shown in FIG. 5 as channel 32. LA Electrode circuitry is replaced by the RL circuitry.

Controller 20 next electronically switches the RA input circuitry in the ECG instrumentation amplifier with the RL output drive circuitry. The LA-LL (channel III) measurement orientation is show in FIG. 5 as channel 33. RA Electrode circuitry is replaced by the RL circuitry.

The RL drive circuitry sequentially connects from the LL to LA to RA so the Noise cancellation system functions without the fourth RL electrode being necessary. Once the data has been acquired for Lead I, channel 31, and Lead II, channel 32 then Lead III, channel 33 can be derived or measured directly. This is possible because Einthoven's Law states that I+(−II)+III=0. The equation can also be written I+III=II. It is written this way (instead of I−II+III=0). Therefore Lead III is Lead II−Lead I. Now the derived channels, channels 34, 35, and 36 can be calculated:

channel 34, $aVR$ (Lead $I$+Lead $II$)/2 channel 35, $aVL$ Lead $I$−(Lead $II$/2)

channel 36, $aVF$ Lead $II$−(Lead $I$/2)

Lead $III$ Lead $II$−Lead $I$

Using only 3 electrodes, electrodes 16A, 16B and 16C it is possible to derive 6 channels (Limb leads & derived leads) of data with the noise cancellation (ground) effect of a virtual dynamic RL electrode.

All ECG signals will be analyzed real-time by the internal algorithm of controller 20. Upon determination of an arrhythmic or patient-activated event such as by activation of event button 38, composite ECG data 39 will be wirelessly transmitted to a remote Monitoring Center such as monitoring center 12 for additional analysis and intervention. If cellular transmission is not possible, the event will be stored for future cellular/TTM/base station transmission such as through conventional phone 40 or base station 41.

Monitoring device 10 will be equipped with a service center lab changeable flash-based memory 42 in order to record the receiving signal coming from the sensor and to allow pre and post processing options through the use of this memory and a mobile database of ECG data and corresponding event markers. The database will facilitate query and retrieval of specific ECG based on event information, time and date, or other data as desired.

Remote ambulatory cardiac monitoring system 10 will automatically transmit the recorded ECG, via cellular technology, to a Remote Management System but will also allow patients to use a land line such as phone 40, plugged into a base station such as base station 41 or held to the MCT Device in a standard Trans-telephonic way (TTM) as illustrated in FIG. 1, to transmit the data in the case where cellular transmission is not possible.

Six elements generally influence physicians' decision on which provider to use for a particular ECG monitor:

Compliance: Ensure greatest amount of quality ECG for analysis

Higher Diagnostic Yield: Provide most clinically-relevant information

Technology: Reliable transmission, easy to use, less patient intervention

Reimbursement: highest reimbursement rates for Partner Physicians

Innovation and fashion: Best solution offered for arrhythmia detection and transmission, including continuous storage and monitoring. Engaging new technology Device Overview Remote ambulatory cardiac monitoring device 10 is a battery-powered, portable and ambulatory, multi-purpose ECG device capable of serving as (1) a resting 12-lead EKG (2) a multi-day Holter recorder and (3) a Mobile Cardiac Telemetry (MCT) device with real-time arrhythmia analysis and a cellular modem.

Cardiac monitoring device 10 is designed to be operated by both patients and medical professionals and has two user-interfaces to address each type of user. It can be operated through touch screen 18 and alternatively using 5-button keyboard 44 with complete functionality by either method.

Cardiac monitoring device 10 has four functional modes of operation: resting 12-lead EKG (medical professionally only); 15 day Holter recorder (patient and medical professional interfaces); 30 day MCT operation (patient, medical professional and service center interfaces); and a USB data transfer mode to download the data stored in memory to a personal computer for long term storage and to perform a more extensive analysis (medical professional only). The built-in cellular modem technology allows patient demographic and scheduling information to be "pushed" from an EMR or HIS system to cardiac monitoring device 10. Conversely, the results can automatically be sent back to same electronic management system to a 24-hour monitoring service facility.

Cardiac monitoring device 10 is "smart," automatically adapting to its intended purpose by detecting the EKG lead set inserted. It also provides embedded video tutorials on hook-up specific to the modality and can also provide real-time ECG arrhythmia detection using its built-in hardware DSP engine in any mode: resting 12-lead EKG; Holter; or MCT.

12-Lead EKG Mode:

Cardiac monitoring device 10 can function as a 12-lead EKG with a special 10-wire, clip, electrode cable lead set. It can be set in "Capture Only" mode or "Capture & Stream" mode.

"Capture Only" mode allows the operator to acquire data in monitor or diagnostic quality mode and store up to 1024 patients EKG on the device. The EKG can later be transmitted wirelessly or downloaded directly via USB to central cardiovascular system computer running receiving and analysis software 46.

The system is intended as a mobile device which can be carried to the patient in a medical office or home environment. Each EKG is displayed on display 18 which may be any suitable touch screen display such as a 3.2" TFT color display in high-resolution and all 12 channels are able to be viewed. There is no EKG interpretive analysis in this mode.

If in the "Capture & Stream" mode, cardiac monitoring device 10 will operate as in "Capture Only" but also send the EKG wirelessly via 802.15.4 transceivers to the central cardiovascular system PC. Cardiac monitoring device 10 can deliver 3, 6, 12 EKG's, interpretive (continued) analysis and vector loops where the data may be viewed, printed, and stored. Additionally, the data is analyzed in the PC using automated ECG analysis and interpretation software library 47.

Holter Mode:

Cardiac monitoring device 10 can function as a Holter with a 3-wire, 5-wire, or 10-wire, snap, ambulatory, electrode cable lead set. It can be set to convert to MCT (30 day ambulatory monitoring) mode automatically if the Holter is negative after 24 or 48 hours. It can be programmed to record 1, 2, 3, or 12 leads up to five days. There are two user-interfaces available: one designed for the medical professional (Tech Mode) which allows recording configurations to be set and; another for the patient (Patient Mode) with a simplified interface allowing events and symptoms to be annotated within the device. There is also a third user-interface where low-level system settings can be changed intended for system administrators (Admin Mode). Cardiac monitoring device 10 also contains hook-up diagrams and instructional videos to aid in assisting to properly prep and place the electrodes properly depending on the EKG lead set being used. Additionally, monitoring system 1 will perform an impedance test, as discussed above, of the electrode cable currently connected for validation of the electrode connection. The impedance test quantifies the resistance of each electrode connection and can compensate for degrading connections that occur over time and also provides the ability to detect an electrode off condition. After connection of the electrodes, all channels of ECG can be reviewed on display screen 18 by a medical professional.

The device screen is normally blank during recording but will show the time and date if a key is pressed along with a message stating "Recording". If "Event" button 29 is pressed, the device will present a drop-down menu for both symptoms and activities. The user may add menu items with the built-in virtual keyboard through touch screen display 9 if desired. The patient also has control over the screen brightness, speaker volume, and the LED indicator.

Furthermore, the patient is not permitted to turn off the device in Holter mode. If the "Power" button is held in for more than five seconds, a special "Tech Mode" key prompt (EVENT-SELECT), only known to the medical technician, will need to be entered to complete the power down function.

The Holter data is also processed and analyzed software library 47.

MCT/Event Mode:

Cardiac monitoring device 10 can also function as a MCT device with a 3-wire, snap electrode, ambulatory cable lead set such as cable 16 of FIG. 1. There are two user-interfaces: one designed for the medical professional which allows recording configurations to be set (Tech Mode) and another for the patient with a simplified interface (Patient Mode) allowing events and symptoms to be annotated within the device and control over the screen brightness, speaker volume, and the LED indicator. There is also a third user-interface where low-level system settings can be changed intended for system administrators (Admin Mode) including patient enrollment, downloading all MCT data, and clearing all memory.

As in Holter mode above, MCT/Event mode also provides hook-up diagrams and instructional videos as well as performing an impedance test. After the electrode connection in MCT/Event mode, all channels can be reviewed on the screen. If a patient electrode connection is performed, no ECG is presented; only a good or bad electrode connection indication message.

Whenever monitoring device 10 is powered up, the patient enrollment is verified and must be confirmed before the device may be used.

The device screen is normally blank during recording but will show the time and date if a key is pressed along with a message stating "Recording". If event button 38 is pressed, device 10 will present a drop-down menu for both symptoms and activities. The user may add menu items with the built-in virtual keyboard if desired. The system will use the display screen, and LED indicator, and audible alarms to notify the user of any messages including a phone number to make a voice call to the 24-hour monitoring service facility. The service may also post messages for the patient.

Cardiac monitoring device 10 is programmed with preset triggers and alarms for sinus bradycardia [based ventricular rate], sinus tachycardia [based on ventricular rate], A-Fib, pauses, and heart-block. If triggers are made then the event is just stored in memory and downloaded at the end of the study. If an alarm is made, the event is sent to a 24-hour monitoring service facility via the cellular modem. The service facility may also adjust the triggers and alarms remotely.

Controller 20 is also configured to interact with software algorithm such as algorithm 55 to cross check each alarm trigger before initiating an alarm. Using the sequential connection to data channels discussed above, an alarm trigger from a data channel will be checked using one or more other data channels to verify the validity of the alarm trigger. The verification cross-check prevents false positive alarms.

In the case where there is no extended cellular coverage, there is a TTM method provided to send events by a conventional (wired) telephone which requires no disconnection of the EKG lead set.

Furthermore, the patient is not permitted to turn off the device unless the "Power" button is held in for more than five seconds; a software confirmation is made by the user to complete the power down function. This would normally be done to perform battery charging, to bathe or change electrodes.

USB Connection Mode:

The USB connection mode is performed by medical professionals to download data from the device or to program the internal settings including patient enrollment. Patients are not permitted to enter this mode.

Hardware Description

Referring now to FIG. 3, the design of cardiac monitoring device 10 is based on microprocessor 48 such as an Atmel AT92SAM9G20 ARM 9 providing very low power consumption, (50 mA with all internal peripherals active) and a Field Programmable Gate Array (FPGA) controller 20. Any suitable microprocessor and gate array may also be used.

Controller 20 controls the functionality of remote ambulatory cardiac monitoring device 10 at the lowest level. There are several modules within the system controller 20 and external to the controller. External components include; the ECG Amplifier, the Analog to Digital Converter, the Digital Pots for programming offset and gains to the ECG amplifier, 3.2"TFT color Display, a keyboard and touch screen interface for the display, a Real Time Clock, a ZIGBEE, 802.15.4 interface, a BLUETOOTH interface, and Accelerometer interface, a Cell Phone interface, Cellular SIM card, SDHC flash memory, Power control circuit, Speaker, Microphone, RGB LED indicator, Event and Power Buttons, and microprocessor 48.

Inside system controller 20 there are also a number of modules. They are the Data Acquisition Module, the Processor Decode module, the SDRAM controller module, the Digital Pot control module, the Hardware Watchdog module, the Video Control module, the ZIGBEE, Control module, the BLUETOOTH Control module, the Accelerometer Control module and the Cell Phone Control module. Each of these modules has the appropriate Register sets to allow total control via microprocessor 48.

ZIGBEE transceiver (802.15.4)
    BLUETOOTH transceiver
    Accelerometer
    Cell phone/GPS
    Video Controller
    Touch panel interface.
    ECG Data Acquisition
    Battery monitor
    Digital POTS interface
    GPIO interface.
    DSP core interface
    8051 secondary Microprocessor core
    Speaker/Microphone interface
    SDRAM
    RGB LED registers & control
    Keyboard button controller
    System decoder
    Resource State Machine & 8051 Arbiter
    8051 Local decoder & Timing Generator
    System control & Status Registers
    I2C Serial modules
    DCM Clock Synthesis
    Real-Time Clock controller
    Byte swapper
    Watch-Dog Timer Control
    Refresh Controller
    SRAM Controller The selection of a suitable processor as microprocessor 48 is based on the integration of fast ROM and RAM memories and a wide range of peripherals. A suitable processor will embed a USB Device Port and a USB Host controller. It may also integrate several standard peripherals, such as the USART, SPI, TWI, Timer Counters, Synchronous Serial Controller, ADC and Multimedia Card Interface. Microprocessor 48 should include a maximum of six concurrent high bandwidth 32-bit busses, and it should also feature an external bus interface capable of interfacing with a wide range of memory devices.

System controller and hardware accelerator block is directly connected to the External Bus Interface of microprocessor 48. Controller 20 is the interface controls all aspects of hardware not integrated into the processor. The following blocks are implemented internal to the controller, and all control and data transfers are via memory mapped I/O for setup, control, and processor data transfers.

Acquire Module. This module controls all aspects of the data acquisition functionality of the design. This module is responsible for the acquisition Channel List Control, Frequency of Scan, Transfer Interrupts, Interrupt Threshold Control, Analog To Digital SPI interface control, Conversion Control, and houses the buffering RAM that feeds the SDRAM Interface block.

Local Decoder. This module is responsible for the decoding of processor accesses to all Read/Write registers accessible to the local processor. It generates all timing and direction control to all modules within the CORE system controller.

Memory Controller. This module directly controls the local SDRAM in all aspects. The local refresh timer, SDRAM power down and power saving control, local DMA transfers between the Acquire block and the SDRAM, Processor access to the SDRAM, (both in random access and FIFO mode access), arbitration control between the DMA requests, Video data requests, and the local processor accesses, and all addresses generated to the SDRAM.

Local Watchdog Timer. This module is programmable for general purpose use in timing for whatever type of wakeup might be needed based on time.

Digital Pot Controller. This module controls all SPI accesses, Digital Pot selection, timing control, and registering of all processor accesses to and from the Digital pots.

BLUETOOTH Controller. This module interfaces to the BLUETOOTH hardware.

ZIGBEE Controller. This module interfaces to the ZIGBEE hardware.

Video Controller. This module controls the LCD accesses by the processor, the raster scan, video data access. All timing generation and sequencing is controlled from this module to present whatever graphics are required.

Touch Screen Interface. This module controls the capacitive virtual button interface that allows the user access to setup and control of the hardware.

Accelerometer Interface. This module is a direct processor access to the 3 axis accelerometer so the display screen orientation flips on position and detects patient position.

Operations

Remote ambulatory cardiac monitoring system 10 is a multi-purpose ECG recorder based on a modular approach. Each requirement of functionality of the design is isolated in its own module, and has a standard intercommunication architecture with other modules of functionality, and the local processor. At the highest level of description, there are several modules within gate array controller 20, and external to the gate array. There are the ECG Amplifier, the Analog to Digital Converter, the Digital Pots for programming offset and gains to the ECG amplifier, a capacitive touch sense interface for a from panel, the front panel itself, a Real Time Clock, a ZIGBEE interface, a BLUETOOTH interface, and Accelerometer interface, a Cell Phone interface, and a processor interface are all external to the gate array. Gate array controller 20 controls all of these above mentioned modules that are external to the gate array.

Inside gate array, controller 20, there are also a number of modules. They are the Data Acquisition Module, the Processor Decode module, the SDRAM controller module, the Digital Pot control module, the Hardware Watchdog module, the Video Control module, the ZIGBEE Control module, the BLUETOOTH Control module, the Accelerometer Control module and the Cell Phone Control module. Any other suitable control module may also be added for additional functionality such as blood pressure module 49 which captures blood pressure data using an ambulatory blood pressure cable. Each of these modules has the appropriate Register sets to allow total control via the local microprocessor.

The design of controller 20 is totally synchronous and supports a single software controllable clock rate. There are many different VHDL modules in this design.

Top Level Module (holter_top.vhd)

This is the top level VHDL module. It is a wrapper for all of the other modules listed above. This module is responsible for all port mapping of sub-modules. It also contains the system control register, the potentiometer select register, write/read strobe generation for I/O, The refresh timer, processor transaction flow control, and reset synchronization. All other modules to follow, are instantiated within this module.

Local Decode Module: (1cl_dec.vhd)

This module is responsible for the decoding local processor accesses to the FPGA. It is capable of up to 256 word only locations, (16 bits). The read/write strobe generation is done in the top level module to be used in conjunction with the output of this module. This decode is based on the activation of io_acc, signal by hardware, and the processor request for read or write. This module also decodes the address space for the SDRAM when CS7 is active. An SDRAM access is only decoded here, and not acted upon. The action is when the SDRAM module sees the decode of SDRAM space. The decodes are based on a simple 3 state machine.

1. Idle_state: This is where the state machine spends most of its time until an access to the decode module is sensed. When in this state, the hardware is looking for an I/O access. This is done with a comparator. Once detected, the io_acc signal goes active to the state machine, and forces the state machine to put out the hold signal to the processor during the transition to the next state, decode1. It also latches the chip select lines, and the lower 9 down to 1 bits of address for decode1.

2. Decode1: This state is entered one clock after the detection of the leading edge of an I/O access. Bits 9 down to 1, (8 bits), are then fed into a look-up table for decode, the proper decode enables are activated to the rest of the FPGA, and is unconditionally sent to the next state, decode2.

3. Decode2: This state does an immediate release of the io_hold generated on transition from the idle state to decode1. The io_hold signal is also used by the top level module to form the trailing edge of a write strobe if it is a write transaction. During a read transaction, the read strobe is generated for the duration of decode. In either case, decode2 waits for the io_acc to clear as a result of the release of the io_hold signal. It then advances back to the starting point, idle state, as soon as the processor terminates the transaction. Transaction termination is based on the negation of all Chip Selects.

Data Acquisition Module: (acquire.vhd)

This module controls, (after programming), all aspects of the data acquisition sequence.

The major blocks within this module are:
1. Scan Sequencer
2. Programmable clock divider to program the acquisitions/sec
3. Processor interface
4. A2D SPI interface
5. Pot Selection
6. Wake Up Count Register
7. Memory Threshold Register
8. DMA Count Register.
9. A2D Mux Address
10. Calibration Voltage Select
11. Input Select
12. ADC Pot Select
13. Wake Up Interrupt Generation
14. A2D Converter control
15. A2D SPI Data accesses
16. Conversion Frequency
17. 1DMA transfers to SDRAM requests Scan Sequencer The Scan Sequencer is made up of a 16×5 bit RAM that holds the following control:
1. Channel to be converted, (bits 3:0)
2. End Sequence Flag, (bit 4)
3. Processor Multiplexer Address
4. Data acquisition sequence address After the processor loads the desired address into the Processor Multiplexer Address register, the required processor access location is setup. When a decode of the scan ram sequencer is decoded on a processor access, the value of the Processor Multiplexer Address is sent to the address inputs of the scan ram. The Data transaction (read/write), will take place to the channel location set up previously in the Processor Mux Address register. This location is one of 16 channels feeding the Analog to Digital Converter addressed by the Scan Ram.

The Scan Ram Sequencer is simply a four bit counter that increments after every scan. The address, (count), comes from the Scan Sequencer logic when running. If location 0 of the scan ram wanted to scan channel 5, then the processor would set up the Processor Mux Address register to 0, and write a 5 into that location. The scan list can be programmed to acquire any channel in any order to provide for maximum flexibility This RAM is accessed in two different manners. Either the processor addresses it to read/write the RAM, (Holter_Run='0' and Mux_Ctl_Mode='1'), or the acquisition control state machine scan sequence register, (Holter_run='1').

When in the processor mode of access, the processor accesses this RAM as a Memory Mapped resource. When the local decoder decodes processor access to this RAM, the hardware passes the address in the processor multiplexer address register to the address inputs of the scan ram, along with the lower five bits of the system data bus, (sys_dat) to the data inputs of the RAM, on a write. During a read, the internal sys_data is tri-stated, and the contents of the RAM are put on bits (4:0) for a read access. Based on the read strobe, (rstrb), and write strobe, (wstrb), the data is either read from the RAM to bits (4:0) of the sys_data bus from the address specified in the processor multiplexer address, or a write to the same location from sys_data(4:0).

When running, (Holter_Run='1'), the address presented to the Scan RAM is from the data acquisition state machine, (scan_seq). These accesses are always reads. At the beginning of a convert cycle, just before the conversion command is given to the A2D converter, the address of the scan sequence is presented to the Scan RAM, and its contents are sent to the external analog multiplexer that feeds the input to the A2D converter. After this, on the next clock, the convert command is given. After the conversion, the scan sequence address is incremented with one exception. If bit 4 of the Scan RAM contents is '1' for the address given, after the conversion the scan sequencer is reset to "0000". This restarts the scan list. The Scan list length is programmable. To make the scan list 1 deep, (then it repeats itself), simply set BIT 4 of the data, (channel included in the data). BIT 4 of the output of the Scan Ram directly resets the counter addressing the scan ram. Therefore, bit 4 being set at location zero, will lock the counter at location 0 when running. For a scan list of 2, write BIT 4 of location 1 to a 1. This causes a counter reset when location 1 is accessed allowing the counter to cycle between locations 0 and 1. Writing a 1 to BIT 4 of location OxF makes the Scan list 16 long. The scan list can be programmed to acquire any channel in any order to provide for maximum flexibility. For a scan list of 16, writing the same channel address in all locations would be logically the same as a single length list. All 16 locations would be accessed, but they would all have the same channel #. This is true for any sequence. This allows the setup to scan one channel more times than another during a scan run allowing individual channels to be acquired at different sampling rates.

Programmable clock divider to program the acquisitions/sec

This is a 16 Bit register that counts 100 ns intervals. Loading this register with a 1 would cause an acquisition clock every 200 ns. This is an illegal number and this register should never be loaded with a value of less than the maximum speed of the A2D converter. Resolution is 100 ns. The slowest clock rate is 65535×100 nS, or 1 channel every 6.5546 mS per channel. A scan rate of 1 MHz, (1 channel every microsecond), would load a value of 9 to this register, (0x0009). Clock rate=N+1 (100 ns), where N=value of this register. A value of zero is illegal and will produce undetermined results.

Processor Interface

The Processor interface accepts decodes from the local decoder pertinent to this module of the design. This interface is based on the output of the local decoder module. When the local processor is making an access, the local decoder sends the appropriate decode signals to this interface. The following signals are pertinent to the update/access to the following blocks of this module:

1. Clock Divider Register
2. Acquisition Control Register, (described earlier).
3. Scan RAM
4. Processor MUX Address.
5. Wake Up Count Register
6. Memory Threshold Register
7. DMA Count Register.
8. A2D Data Path
9. A2D FIFO Path
10. SPI Data Path/Control A2D SPI Interface The A2D SPI interface is for the purpose of all local processor to A2D protocol conversion and control. The A2D is an SPI based device that has a 16 bit transfer in either direction. There is a state machine to handle both sides of this interface. On one side of the state machine is the local processor. The local processor sets appropriate bits to the state machine for high level control, and for data writes and data reads. On the other side of the state machine is the A2D Converter SPI Interface. This part of the interface, (acquisition control and translation), is also fed by the Base Time Acquisition clock, (adc_clk), that is a direct derivative of the Programmable Clock Divider described above. Once the local processor asserts the holter_run bit, every adc_clk starts another conversion from the channel addressed from the Scan RAM. This can be confusing due to the fact that the Scan RAM both produces addresses and accepts them for look-up. The address in this discussion is the output of the Scan RAM. This is done with a multiple, (8 state), state machine.

IDLE: This is the state entered after a power up, a reset, or a completion of a conversion. While in this state, the state machine is looking at the holter run bit. This bit is set on the next leading edge of a conversion clock, (adc_clk). At this time the SPI data out pin of the FPGA is driven high to do the CS mode of operation, this forces the busy bit active mode. The state machine then transitions to START CNV.

START CNV: During this state the adc_cnv clock is asserted. This instructs the A2D converter to convert the analog value presented at its input. There are 16 data bits in conversion transfer. The lower 16 bits are converted data and the 17th bit, (busy) is the MSB of the serial chain. Then the next state BUSY_W8 is entered.

BUSY_W8: Upon entering this state, the state machine waits for the data out of the SPI, (SDO from the ADC) to go to a zero state. This signifies the negation of the busy signal from the previous convert pulse, (ADC_CNV). Once this is detected, the state machine negates A2D_SDI, and asserts the SPI_CLK signal, shifting out the busy bit. The state machine then transitions to the BUSY_SHIFT state.

BUSY_SHIFT: Upon entering this state, the state machine negates the SPI_CLK, and forms the trailing edge of the first SPI_CLK. There is one system clock skipped to allow for minimum pulse width of the ADC SPI interface. After this delay, the state machine asserts the leading edge of the next pulse. We then transition the BUSY_SHIFT1 state.

BUSY_SHIFT1: This state, when entered skips one machine clock to not violate the minimum pulse width of the SPI_CLK. After this delay, SPI_CLK is negated and the state machine transitions to GET_DATA1.

GET_DATA1: This state, when entered again skips one machine clock to allow for setup time from the SPI_DATA pin, but at the same time negates the SPI_CLK. After this delay the internal shift count is incremented, and the data from the SPI is shifted into the LSB of the serial to parallel register, and at the same time, the MSB is shifted out to the SPI interface. The information shifted into the serial to parallel register is a function of the command. If the command is a read command, the register specified in the command is accessed. If it is a write command, the command word is written right back into the serial to parallel register as a function of the SPI interface of the A2D converter. On this same clock edge, the SPI_CLK is again asserted, and the transition to GET_DATA2 takes place.

GET_DATA2: Upon entering this state, the SPI CLK is negated. On the same clock edge, the shift count is checked for 16. If the result is false, the state machine transitions back to GET_DATA1. If the count is 16, the load a2d fifo signal is activated, (LD_A2D_FIFO). This causes a shift of the parallel word just captured, and the state machine transitions to TERMINATE1.

TERMINATE1: This state negates the SPI_CLK signal and jumps to the IDLE state.

Algorithm Specifications

This section shall define the functional requirements of the system and sub-system of controller algorithm 20A.

Sinus Pause:

A sinus pause will be documented whenever a predetermined period of time elapses without a QRS complex of any morphology. This algorithm will not discriminate between a Sinus Pause and Sinus Block as this interval timer will be based on R-Wave to R-Wave intervals. The programmable time period for a Sinus Pause is 1.5, 2.0, 2.5, 3.0, 3.5 or 4.0 seconds, with 2.0 seconds being the factory default setting. The detection of Sinus Pause can be turned on or off without affecting any of the other arrhythmia settings.

Bradycardia:

Bradycardia occurs when the patient's heart rate goes below a preset limit. The heart rate for calculating Bradycardia is based on a 6-beat rolling average, a 10-beat rolling average or a 16-beat rolling average that can be selected in the configuration software. The factory default setting is a 10-beat rolling average. The programmable heart rate settings for Bradycardia are 30, 35, 40, 45, 50, 55, 60, 65 and 70 beats per minute (BPM) with 40 BPM being the factory default setting. The detection of Bradycardia can be turned on and off without affecting any of the other arrhythmia configuration settings.

Bradycardia Time Offset:

Bradycardia within a patient can often go below the preset limit when sleeping. In order to accommodate for this phenomena, the heart rate for calculating Bradycardia can be lowered by 5, 10, 15, 20 beats per minute (BPM) with 10 BPM being the factory default. The selection for window set in Bradycardia will be utilized for this setting. The Bradycardia Time Offset can be turned on and off without affecting any of the other arrhythmia configuration settings and is OFF by default.

Tachycardia:

Tachycardia occurs when the patient's heart rate goes above a preset limit or in the event of 3 or more sequential Ventricular beats. The heart rate for calculating Tachycardia is based on a 6-beat rolling average, a 10-beat rolling average or a 16-beat rolling average that can be selected in the configuration software. The factory default setting is a 10-beat rolling average. The algorithm will calculate the rate for both Normal and Ventricular beat such that it will detect Sinus Tachycardia, Supraventricular Tachycardia and Ventricular Tachycardia. The programmable heart rate settings for Tachycardia are 70, 75, 80, 85, 90, 95, 100, 105, 110, 115, 120, 125, 130, 135, 140, 145, 150, 155, 160, 165, 170, 175, 180, 185, 190, 195, and 200 beats per minute (BPM) with 100 BPM being the factory default setting. The detection of Tachycardia can be turned on and off without affecting any of the other arrhythmia configuration settings.

Atrial Fibrillation:

The AFib detection algorithm uses a probability density function (PDF) method based on a reconstructed attractor of R-R intervals. By constructing the PDF of distance between two points in the reconstructed phase space of R-R intervals of normal sinus rhythm (NSR) and atrial fibrillation (AF), the distributions of PDF of NSR and AF R-R intervals have significant differences. By taking advantage of their differences, a characteristic quantity parameter kn, which represents the sum of n points slope in filtered PDF curve, is used to detect both NSR and AF R-R intervals. AFib detection is based on dynamically created PDFs and is not dependent on reference PDFs from known published databases from MIT-BIH, AHA, etc. Those databases were, however, used in preliminary algorithm development to determine the optimal embedding dimension m, the characteristic quantity Kn, and the slope number used by the algorithm for optimal performance as described below.

Stage 10 consists of Phase Space Reconstruction. The R-R interval is just one observable variable from the multi-variable cardiac system. According to Takens' embedding theorem, the state of a dynamic system can be represented in a reconstructed phase space by time delay embedding. Taken's theorem guarantees that the dynamic characteristics of the real physiological) and the reconstructed system are the same. Therefore, it is possible to reconstruct the phase space of the original cardiac system from the R-R intervals while preserving the system dynamics. If x(i) is an element of the R-R intervals vector X, then a reconstructed vector Yi is introduced as $$Yi=[x(i), x(i+\tau), \ldots, x(i+(m-1)\tau)] \quad \text{(Equation 1)}$$

where $\tau$ is the time delay and m is the embedding dimension. The reconstructed vector Yi represents a point in the m-dimensional phase space. By reconstructing the R-R intervals and investigating the structure of the reconstructed attractor, it is possible to provide more information and new diagnostic potential of the analyzed cardiac system. The phase space reconstruction consists of 5 dimensions (embedding dimension m=5) based on a 40 beat window ([40,5] phase-space array) to a 100 beat window ([100,5] phase space array). A 40-beat windows gives speed the priority (real-time application) where moving towards a 100-beat window gives accuracy the priority (real-time application with DSP assist or PC-based system).

Stage 11 constructs the Probability density function. The basic idea behind the PDF method is to construct the correlation function $C(r,m,\tau)$. $C(r,m,\tau)$ describes the probability that the distance between arbitrary two points Yi and Yj in the phase space is shorter than distance r. $C(r,m,\tau)$ can be written as $$C(r,m,\tau)=2/(N(N-1)) \Sigma_{(i=1)}^{(N-1)} \Sigma_{(j=i+1)}^{N}$$
$$[\theta(r-\|Y_i-Y_j\|)] \quad \text{(Equation 2)}$$

where N is the number of phase space points, symbol $\|\cdot\|$ represents the Euclidean distance, and $\theta(x)$ is the Heaviside unit-step function which is defined by $$\theta(z)=\{1 \ Z\geq0\} \ \{0 \ Z<0\} \quad \text{(Equation 3)}$$

Equations (1)-(3) are essential steps of the Grassberger and Procaccia (GP) method to calculate the correlation dimension. The determination of the correlation dimension from R-R intervals are commonly used for gaining information about the nature of the underlying cardiac dynamics. Since the correlation function $C(r,m,\tau)$ has a maximum of 1, minimum of 0 and is a continuous distribution function, we define the probability density function as $$p(r, m, \tau)=dC(r, m, \tau)/dr$$

The PDF is now used for the analysis of the reconstructed attractor structure. A low pass filter (IIR Butterworth type, eight orders with cutoff frequency 1.5 Hz) is used to filter the high frequency fluctuating components of the PDF curves. After low pass filtering, PDF curves of short-time R-R intervals have a near Gaussian distribution.

Stage 12 calculates the Characteristic Quantity kn from the Receiver Operating Curve (ROC). rmin, rtop and rmax are defined as the abscissas of the starting point, the peak and the ending point of the filtered PDF curves, respectively. The values of rmin, rtop and rmax of NSR R-R intervals are smaller than those of AF R-R intervals. This is due to the fact that the neighboring NSR R-R intervals are more correlated, so points in the reconstructed phase space are more concentrated; whereas the neighboring AF R-R intervals are less correlated, so points in the reconstructed phase space are more dispersed. However, rmin, rtop and rmax are not good indexes for differentiating AF from NSR. Therefore, the slope information of the filtered PDF curves is used to improve the detection precision $$k\_n=[(PDF)] \text{ filtered}/rmax(n) \times 100$$

rrmax is divided evenly into 100 segments and d is the length of each segment. PDFfiltered (n) is the value of the nth point in the filtered PDF curve. Naturally, the 0th point in the filtered PDF curve is O. Therefore, kn denotes the sum of the slope of n points in the filtered PDF curve. The characteristic quantity kn fully takes advantage of the following characteristics of filtered PDF curves:

(1) most of the values of rmax of AF are bigger than those of NSR;

(2) most of the values of rtop of AF are bigger than those of NSR, which means filtered PDF curves of NSR rise much faster than those of AF;

(3) most of the values of rmin of AF are bigger than those of NSR, i.e., among the n points slope, AF has more small slope than NSR. All these characteristics make the value of kn of NSR bigger than that of AF as long as n is carefully selected.

Stage 13 uses Kn to determine whether the PDF represents values of NSR or AFib. If a 40 beat window is used then the number of points used to determine the slope is 20 and a threshold of 210 for Kn is used to determine whether the PDF value is characteristic of AFib of NSR. If a 100 beat window is used, the number of the slope points n is 10 and 78 is used for the threshold of Kn. The same concept applies to 60 and 80 beat windows.

Thus, while the preferred embodiments of the devices and methods have been described in reference to the environment in which they were developed, they are merely illustrative of the principles of the disclosure. Other embodiments and configurations may be devised without departing from the spirit of the disclosure and the scope of the appended claims.

I claim:

1. A remote ambulatory cardiac monitoring system for acquiring ECG signals, the system comprising:
    an ambulatory housing configured to be worn by a patient during operation of the ambulatory cardiac monitoring system;
    a microprocessor for controlling the remote ambulatory cardiac monitoring system, and the microprocessor is disposed within the ambulatory housing;
    an electrode for sensing ECG signals and the electrode being in communication with the microprocessor and the electrode connected to the ambulatory housing; an integrated cellular module connected to the microprocessor and disposed within the ambulatory housing and the integrated cellular module is not disposed within a separate housing of a separate device, wherein the integrated cellular module transmits ECG signals for remote review;
    a controller connected to the microprocessor and disposed within the ambulatory housing, the controller switches the functionality of the remote ambulatory cardiac monitoring system by causing the microprocessor to initiate one of a plurality of different modes including an EKG/ECG mode, an ECG Holter mode and an MCT/Event mode, wherein the controller switches the functionality of the remote ambulatory cardiac monitoring system to the MCT/Event mode when three electrodes are in communication with the microprocessor.

2. The system of claim 1, further comprising a non-transitory computer readable medium associated with the microprocessor, the non-transitory computer readable medium including instructions to perform the plurality of different modes.

3. The system of claim 1, further comprising a cable socket disposed on the ambulatory housing and connected to the electrode.

4. A remote ambulatory cardiac monitoring system for acquiring ECG signals, the system comprising:
    an ambulatory housing configured to be worn by a patient during operation of the ambulatory cardiac monitoring system;
    a microprocessor for controlling the remote ambulatory cardiac monitoring system, and the microprocessor is disposed within the ambulatory housing;
    an electrode for sensing ECG signals and the electrode being in communication with the microprocessor and the electrode connected to the ambulatory housing; an integrated cellular module connected to the microprocessor and disposed within the ambulatory housing and the integrated cellular module is not disposed within a separate housing of a separate device, wherein the integrated cellular module transmits ECG signals for remote review;
    a controller connected to the microprocessor and disposed within the ambulatory housing, the controller switches the functionality of the remote ambulatory cardiac monitoring system by causing the microprocessor to initiate one of a plurality of different modes including an EKG/ECG mode, an ECG Holter mode and an MCT/Event mode, wherein the controller switches the functionality of the remote ambulatory cardiac monitoring system to the ECG Holter mode when three electrodes are in communication with the microprocessor.

* * * * *